United States Patent [19]

Mestetsky

[11] Patent Number: 5,660,732
[45] Date of Patent: *Aug. 26, 1997

[54] METHOD OF SEPARATING OLEOPHILIC-HYDROPHOBIC MATERIAL FROM WASH WATER

[75] Inventor: Pat A. Mestetsky, St. Charles, Ill.

[73] Assignee: United Laboratories, Inc., St. Charles, Ill.

[*] Notice: The term of this patent shall not extend beyond the expiration date of Pat. No. 5,459,066.

[21] Appl. No.: 420,147

[22] Filed: Apr. 11, 1995

Related U.S. Application Data

[62] Division of Ser. No. 128,061, Sep. 28, 1993, Pat. No. 5,459,066, which is a continuation of Ser. No. 752,369, Aug. 30, 1991, abandoned.

[51] Int. Cl.$^6$ ........................................ C02F 1/00
[52] U.S. Cl. .................. 210/708; 210/728; 210/729; 134/10; 134/20; 252/344; 252/358
[58] Field of Search ........................ 210/632, 702, 210/708, 723, 727, 728, 735, 729; 134/10, 20; 252/344, 358

[56] References Cited

U.S. PATENT DOCUMENTS

| | | |
|---|---|---|
| 2,367,384 | 1/1945 | Tymstra et al. . |
| 3,272,758 | 9/1966 | De Lew et al. . |
| 3,457,168 | 7/1969 | Malmberg et al. . |
| 3,634,227 | 1/1972 | Patterson . |
| 3,740,315 | 6/1973 | Li et al. . |
| 3,880,739 | 4/1975 | Leavitt . |
| 3,948,770 | 4/1976 | Goodrich et al. . |
| 4,146,470 | 3/1979 | Mohan et al. . |
| 4,224,152 | 9/1980 | Lepain . |
| 4,256,605 | 3/1981 | Baker . |
| 4,420,573 | 12/1983 | Fogg et al. . |
| 4,469,603 | 9/1984 | Lepain et al. . |
| 4,512,914 | 4/1985 | Lepain et al. . |
| 4,560,482 | 12/1985 | Canevari . |
| 4,623,468 | 11/1986 | Lepain et al. . |
| 4,830,759 | 5/1989 | Charlier . |
| 4,940,539 | 7/1990 | Weber . |
| 4,992,213 | 2/1991 | Mallett et al. . |
| 5,459,066 | 10/1995 | Mestetsky .......................... 435/266 |

OTHER PUBLICATIONS

Product Bulletin "Zyme Flow Super Concentrate Enzyme-Based Grease Solubilizer—United 555" (#1) (Circa Jan., 1985).

Product Bulletin "Zyme Flow Super Concentrate Enzyme-Based Grease Solubilizer—United 555" (#2) (Circa Oct., 1986).

Product Bulletin "Zyme Flow Super Concentrate Enzyme-Based Grease Solubilizer—United 555" (#3) (Circa Dec., 1986).

Product Bulletin, "Zyme Flow Super Concentrate Enzyme-Based Grease Solubilizer—United 655" (Circa May, 1987).

Product Bulletin "Zyme Flow WWT Super Concentrate Enzyme-Based Grease Pre-Digester—United 655" (Circa Apr., 1988).

Product Bulletin "Zyme Flow Marine Super Concentrate Enzyme-Based Grease Pre-Digester—United 656" (Circa Mar., 1991).

Product Bulletin "Zyme Flow Refinery Super Concentrated Enzyme-Based Grease Pre-Digester—United 657" (Circa Mar., 1991).

"Taking the Bite Out of Filter Buildup, Cost-Effective Filter Remediation", vol. 7, No. 1, *Operations Forum*, Jan., 1990.

"Tertiary, Gravity, Mixed Media Sand Filter Remediation" (Circa Mar. 22, 1990).

Laboratory Report, IT Analytical Services, San Jose, CA, dated Mar. 13, 1990.

*Primary Examiner*—Robert Popovics
*Attorney, Agent, or Firm*—Andrus, Sceales, Starke & Sawall

[57] ABSTRACT

A method of separating oleophilic-hydrophobic material from wash water is disclosed. The method comprises the steps of mixing with the wash water, either alone or in combination, about 30–2100 ppm of a surfactant having the formula:

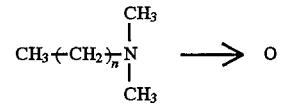

where n is 6–20; and about 1–200 ppm of an enzyme selected from the group consisting of proteases, amylases, lipases, cellulases, pectinases and mixtures thereof. The mixture of wash water surfactant and/or enzyme is then permitted to stand for a time sufficient for the oleophilic-hydrophobic material to separate.

10 Claims, No Drawings

METHOD OF SEPARATING OLEOPHILIC-HYDROPHOBIC MATERIAL FROM WASH WATER

This is a division of Ser. No. 128,061 filed Sep. 28, 1993 now Pat. No. 5,459,066, which in turn is a continuation of application Ser. No. 07/752,369, filed Aug. 30, 1991, and now abandoned.

BACKGROUND OF THE INVENTION

The present invention is directed to the separation of oleophilic-hydrophobic material such as oil, grease, metal chippings, dirt, and the like from wash water.

Industrial machines contain metal parts that move "against" one another, as for example, gears, drive chains, bearings, etc. To aid the movement of these machine parts and to extend their useful life, lubricants such as oils and greases are oftentimes utilized. However, over a period of time, lubricants begin to lose their effectiveness due to the accumulation of dirt and dust, as well as from the severe conditions of heat, pressure, and friction, to which the lubricants are oftentimes subjected. Additionally, the metal machine parts suffer from wear despite the presence of such lubricants. As the metal parts wear, metal chippings become dispersed throughout the lubricant further soiling and detracting from the useful life of the lubricant. To assure that the machinery operates at an optimum level, the soiled lubricant must eventually be removed and replaced.

One such method of removing the soiled lubricant from industrial machinery is by cleaning the machinery with an aqueous cleaning composition containing a mixture of surfactant and enzyme. The waste-product of this cleaning procedure (i.e. the wash water) contains the soiled lubricant which consists of oil, grease, dirt, metal chippings, and the like, dispersed throughout the aqueous cleaning composition.

According to prior practice, this wash water was disposed of by simply dumping it into the local sewer system. However, local ordinances requiring a reduction in the volume of grease, oil and insoluble solids discharged into municipal sewers are becoming both more stringent and prevalent. Accordingly, it may not be possible to dispose of the wash water in the local sewer system. A potential alternative to disposing the wash water in the local sewer system is to use a waste hauling service. However, where relatively large volumes of wash water are generated, it can become prohibitively expensive to have it hauled away. Ideally, and in accordance with contemporary industrial practice, it would be particularly advantageous if the wash water could be treated so that its oil and water components could be recycled. Accordingly, there is presently a need for a method of treating wash water such that it is recyclable, or in the alternative, more easily and less expensively disposed of.

SUMMARY OF THE INVENTION it has surprisingly been discovered that treating wash water with surfactant and enzyme in appropriate concentrations promotes the stratification of the oleophilic-hydrophobic material dispersed therein. Once stratified, the layers of oil, grease, metal chippings, dirt and the like may then be removed from the wash water according to any of the various methods known by those skilled in the art. This phenomenon is especially advantageous in that, once this oleophilic-hydrophobic material is removed from the wash water, the water, oil and grease components may be recycled. Alternatively, the wash water may be sufficiently clean to dispose of in the local sewer system. Finally, the dirt, metal chippings, and the like may be recovered from the wash water and, due to the reduced volume, less expensively disposed of.

In one aspect of this invention a method of separating oleophilic-hydrophobic material from wash water is provided. According to this method, 30–2100 ppm surfactant is mixed with wash water wherein the surfactant has the formula:

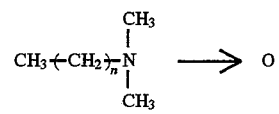

where n is 6–20.

In another aspect of this invention, about 1–200 ppm enzyme selected from the group consisting of proteases, amylases, lipases, cellulases, pectinases and mixtures thereof is mixed with the wash water.

In another aspect of the present invention the surfactant is selected from the group consisting of lauryl dimethyl amine oxide, stearyl dimethyl amine oxide, myristyl dimethyl amine oxide and mixtures thereof.

In yet another aspect of this invention, both surfactant and enzyme are mixed with the wash water.

All concentrations set forth herein are expressed in parts per million (ppm) based on the total solids/volume of the wash water including the contribution to the total solids/volume by the surfactant and enzyme.

As used herein, the phrase "oleophilic-hydrophobic material" refers to oleophilic or hydrophobic substances such as oil, grease, dirt, metal chippings or the like. Furthermore, the term "wash water" as used herein refers to water which contains a quantity of oleophilic-hydrophobic material. In actual practice, the wash water because of the manner in which it contacts the article to be cleaned, such as by spraying or pumping, is agitated or mixed.

DETAILED DESCRIPTION OF THE PRESENTLY PREFERRED EMBODIMENTS

Aqueous cleaning compositions containing a combination of surfactant and enzyme have been used in the past to remove grease, scum, oil and coal dust from various industrial machines and processes according to a dispersion mechanism. Surfactant molecules have both hydrophilic and oleophilic groups. According to the dispersion mechanism, an oleophilic group on the surfactant will attach to a particle of oil, grease, dirt or the like and pull it into dispersion by the attraction of the surfactant's hydrophilic group for the water with which it is added. The dispersion is maintained by the action of the surfactant's hydrophilic groups. The hydrophilic groups on different surfactant molecules repel each other, which necessarily results in the repulsion between the particles of oil, grease, dirt and the like. When the wash water is removed from the industrial machine or process, the dispersion of these materials is removed as well.

It has surprisingly been discovered that certain surfactants and enzymes, which are used as dispersants in removing oleophilic-hydrophobic materials according to the previously discussed process, no longer behave as dispersants at certain concentrations. Instead, these surfactants and enzymes manifest the opposite behavior acting as stratifying agents capable of stratifying the oleophilic-hydrophobic particles of oil, grease, dirt, and the like. The surfactants and enzymes used in the method of this invention promote the stratification of the oleophilic-hydrophobic material present in the wash water according to its density. Accordingly, less dense substances relative to water such as oil will form a top layer, which can then be removed from the wash water. For example, the oil can be removed using normal waste clarifiers with surface skimming, or by dissolved air flotation devices. The recovered oil can then either be recycled or, due to its reduced volume, less expensively disposed of. Conversely, the more dense substances relative to water form a bottom layer which can be removed from the wash water and relatively inexpensively disposed of. Finally, the middle water layer may be recovered and recycled or potentially disposed of in the local sewer system.

In one embodiment of this invention, about 30–2100 ppm surfactant is mixed with the wash water. The surfactant has the formula:

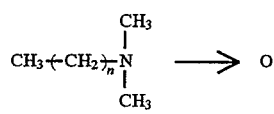

where n is 6–20. Preferably, about 100–800 ppm surfactant is mixed with the wash water. Even more preferably, 100–500 ppm, and most preferably 100–300 ppm surfactant is mixed with the wash water. Preferably, the surfactant is selected from the group consisting of lauryl dimethyl amine oxide, stearyl dimethyl amine oxide, myristyl dimethyl amine oxide, and mixtures thereof. The most preferred surfactant is lauryl dimethyl amine oxide. The mixture of surfactant and wash water is allowed to stand for a time sufficient for the stratification of the oleophilic-hydrophobic material dispersed therein.

In another embodiment of the present invention, about 1–200 ppm enzyme is mixed with the wash water. More preferably, about 1–100 ppm, and even more preferably 1–50 ppm, enzyme is mixed with the wash water. Most preferably, 10–30 ppm enzyme is mixed with the wash water. The enzyme is selected from the group consisting of proteases, amylases, lipases, cellulases, pectinases, and mixtures thereof. More preferably, the enzyme is selected from the group consisting of bacterial protease from *Bacillus subtilis*, amylase from *Bacillus subtilis*, lipase from *Aspergillus niger*, cellulase from *Aspergillus niger*, pectinase from *Aspergillus niger*, and mixtures thereof. Even more preferably, the method of the present invention utilizes an enzyme mixture of protease from *Bacillus subtilis*, amylase from *Bacillus subtilis*, lipase from *Aspergillus niger*, cellulase from *Aspergillus niger*, and pectinase from *Aspergillus niger*. Most preferably, this mixture of enzymes is obtained from Applied Biochemists, Inc., Milwaukee, Wis. under the trademark "AMERZYME-A-100". The mixture of wash water and enzyme is permitted to stand for a time sufficient to permit the stratification of the oleophilic-hydrophobic material dispersed therein.

In a most preferred embodiment of the present invention, both surfactant and enzyme are mixed with the wash water. The surfactant and enzyme are mixed with the wash water as described above. The mixture of wash water, enzyme and surfactant is permitted to stand for a time sufficient to permit the stratification of the oleophilic-hydrophobic material dispersed therein.

The following examples are not to be construed as limiting the scope of the present invention but are merely provided to illustrate various embodiments.

EXAMPLE 1

Table 1 relates to the ability of surfactant and enzyme, alone and in combination, to promote the separation of oleophilic-hydrophobic material from wash water according to the method of the invention. The surfactants used in this example were obtained from Stephan Chemical, Chicago, Ill. under the trademark AMMONYX-LO (lauryl dimethyl amine oxide); AMMONYX-S0 (stearyl dimethyl amine oxide); and AMMONYX-MCO (myristyl dimethyl amine oxide). The enzyme used in the example is "AMERZYME-A-100" from Applied Biochemists, Inc., previously discussed. The pump oil utilized was Hyvack pump oil available from Boekel Corp., Philadelphia, Pa. The iron powder used was obtained from Seargent-Welch Scientific, Skokie, Ill. The water used was St. Charles, Ill. tap water.

The following chart is helpful in interpreting the data in TABLE 1:

| Description of Layer | Interpretation |
| --- | --- |
| CL YEL (Clear Yellow) | Pump oil layer substantially free of water and iron |
| CLDY YEL (Cloudy Yellow) | Pump oil layer with some water dispersed therein |
| GREY/WHITE | Pump oil layer with some water and minor amount of iron dispersed therein |
| GREY | Pump oil layer with some water and minor amount of iron dispersed therein |
| CLDY GREY (Cloudy Grey) | Water layer with some pump oil and iron dispersed therein |
| GREY/YELLOW | Pump oil layer with minor amount of iron powder dispersed therein |
| BL/YEL (Black Yellow) | Pump oil layer with substantial amount of iron powder dispersed therein |
| BLACK | Iron powder layer |

In control sample (1), to a 100 cc graduated cylinder were added 10 cc pump oil, ¼ teaspoon (tsp.) iron powder and water to 100 cc. No enzyme or surfactant was added. The resulting mixture was inverted thirty times and allowed to stand for five (5) minutes. The top layer was a black/yellow color indicating the presence of an oil layer with iron powder dispersed throughout. The middle layer was cloudy white indicating the presence of water with some oil and iron powder dispersed throughout. The bottom layer was black indicating the presence of iron powder. After testing, the cylinder was extremely difficult to clean, both the oil and iron powder tenaciously clung to the sides of the cylinder.

In samples (2)–(6), (10)–(15) and (38) the procedure of sample (1) was repeated except that surfactant and enzyme were added prior to dilution in the amount shown in the following Table I. After standing for 5 minutes, all of the samples (2)–(6) and (10)–(15) formed layers. Samples (2)–(5) clearly demonstrated superior stratification of the oil as demonstrated by the relatively large clear yellow top layer. Samples (14) and (15) also manifested fairly good stratification. After testing, the cylinders containing samples (2)–(6) and (10)–(15) were easily cleaned.

Samples (7–9) were prepared in the manner of Sample 1, except that in Sample 7 only a surfactant was added, while in Sample 8 only enzymes were added. Sample 9 was a control sample containing oil and iron powder but not a surfactant nor enzymes.

With regard to sample (7) containing 180 ppm surfactant but no enzyme, some stratification was observed. Sample (8) containing 25 ppm enzyme but no surfactant also manifested some stratification. However, sample (9), like sample (1) containing no surfactant or enzyme, had a top layer that was black/yellow, indicating a top layer of oil with iron dispersed substantially throughout.

In control sample (16), an aqueous dispersion of oleophilic-hydrophobic material was made by adding to an electric blender 12.1 cc of pump oil, 140 cc water, and ½ tsp. iron powder and agitating this mixture at low speed for thirty (30) seconds. Thereafter, 15 cc water was added to a 100 cc graduated cylinder. The above described dispersion was then added to the cylinder to a total volume of 100 cc. The graduated cylinder was inverted 5 times and observed after 5 minutes at rest. No separation was observed. Furthermore, it was found that the cylinder containing sample (16) was extremely difficult to clean, the oil and iron powder tenaciously clung to the sides of the cylinder. Samples (17)–(25) were prepared in a similar manner. It can be seen from these samples that various concentrations of the surfactant and enzyme combination promote the stratification of the oil and the iron powder to various degrees.

With regard to samples (26)–(37), an aqueous dispersion was made by adding to an electric blender 40 cc pump oil, 300 cc water, and 1 tsp. of iron powder. This mixture was agitated at low speed for 30 seconds. The surfactant, enzyme and some water were added to a 100 cc graduated cylinder. The above-described dispersion was then added to the cylinder to the volume indicated. The cylinder was inverted 5 times and observed after 5 minutes. With regard to these samples, it can be seen that various concentrations of the surfactant and enzyme combination promote the stratification of the oil and the iron powder to various degrees.

In summary, those samples with clear yellow and cloudy yellow top layers (samples (2)–(5)) or a cloudy yellow top layer (samples (11)–(12) and (14)–(15)) are preferred. Whereas those samples with black/yellow top layers are less desirable (samples (30)–(33)).

TABLE 1

| NO. | SURFACT. TYPE AMMONYX | X= III | SURFACT. CC @ 1.2% | PPM ACTIVE SURFACT. | ENZYME CC @ .05% | PPM ENZYME | OIL CC | % OIL | IRON POWDER | TOTAL VOLUME | TOP | 5 MINUTES SETTLING CC | CENTER | BOTTOM |
|---|---|---|---|---|---|---|---|---|---|---|---|---|---|---|
| 1 | — | | — | 0 | — | 0 | 10 | 10.0 | 0.25 | 100 | BL/YEL | 7 | CLDY | BLACK <5 CC |
| 2 | LO | 11 | 20 | 720 | 20 | 100 | 10 | 10.0 | 0.25 | 100 | CL YEL/CLDY YEL | 8 | CLDY | BLACK <5 CC |
| 3 | LO | 11 | 15 | 540 | 15 | 75 | 10 | 10.0 | 0.25 | 100 | CL YEL-1.5/CLDY YEL-9 | 10.5 | CLDY | BLACK <5 CC |
| 4 | LO | 11 | 10 | 360 | 10 | 50 | 10 | 10.0 | 0.25 | 100 | CL YEL-2/CLDY YEL-8 | 10 | CLDY | BLACK <5 CC |
| 5 | LO | 11 | 5 | 180 | 5 | 25 | 10 | 10.0 | 0.25 | 100 | CL YEL-8/CLDY YEL-1.5 | 9.5 | SL, CLDY | BLACK <5 CC |
| 6 | LO | 11 | 1 | 36 | 1 | 5 | 10 | 10.0 | 0.25 | 100 | V CLDY GERY YEL | 7 | V CLDY | BLACK <5 CC |
| 7 | LO | 11 | 5 | 180 | 0 | 0 | 10 | 10.0 | 0.25 | 100 | V CLDY GREY YEL | 6 | V CLDY | BLACK <5 CC |
| 8 | — | | — | 0 | 5 | 25 | 10 | 10.0 | 0.25 | 100 | GREY | 4 | CLEAR | BLACK <7 CC |
| 9 | — | | — | 0 | — | 0 | 5 | 10.0 | 0.25 | 50 | BL/YEL | 2 | CLDY | BLACK <5 CC |
| 10 | — | | 5 | 180 | 5 | 25 | 5 | 10.0 | 0.25 | 50 | GREY YEL | 3.5 | CLDY | BLACK <5 CC |
| 11 | LO | 11 | 5 | 180 | 5 | 25 | 10 | 10.0 | 0.25 | 100 | CLDY YEL | 4 | CLDY | BLACK <5 CC |
| 12 | LO | 11 | 10 | 360 | 10 | 50 | 10 | 10.0 | 0.25 | 100 | CLDY YEL | 17 | CLDY | BLACK <5 CC |
| 13 | SO | 17 | 10 | 306 | 10 | 50 | 10 | 10.0 | 0.25 | 100 | GREY WHITE | 22 | CLEAR/FLOCS | BLACK <5 CC |
| 14 | MCO | 14 | 10 | 360 | 10 | 50 | 10 | 10.0 | 0.25 | 100 | CLDY YEL | 18 | CLDY | BLACK <5 CC |
| 15 | SO | 17 | 5 | 153 | 10 | 50 | 10 | 10.0 | 0.25 | 100 | CLDY YEL | 14 | CLEAR | BLACK <5 CC |
| 16 | — | | — | 0 | — | 0 | 12.1 | 12.1 | 0.25 | 100 | NO LAYER | 0 | CLDY YEL | NO LAYER |
| 17 | — | | — | 0 | — | 0 | 11.4 | 12.6 | 0.25 | 90 | NO LAYER | 0 | CLDY YEL | NO LAYER |
| 18 | SO | 17 | 10 | 306 | 10 | 50 | 10 | 10.0 | 0.25 | 100 | GREY WHITE | 17 | CLEAR/FLOC | BLACK <5 CC |
| 19 | LO | 11 | 10 | 360 | 10 | 50 | 10 | 10.0 | 0.25 | 100 | GREY | 5 | CLDY | BLACK <5 CC |
| 20 | 1:1 LO:SO | 11:17 | 10 | 333 | 10 | 50 | 10 | 10.0 | 0.25 | 100 | GREY | 8 | CLDY | BLACK <5 CC |
| 21 | LO | 11 | 2 | 72 | 10 | 50 | 10 | 10.0 | 0.25 | 100 | GREY | 12 | CLDY | BLACK <5 CC |
| 22 | LO | 11 | 5 | 180 | 5 | 25 | 10.6 | 10.6 | 0.26 | 100 | GREY | 3 | CLDY | BLACK <5 CC |
| 23 | LO | 11 | 1 | 36 | 5 | 25 | 10.6 | 10.6 | 0.26 | 100 | GREY | 4 | CLDY | BLACK <5 CC |
| 24 | LO | 11 | 2 | 72 | 5 | 25 | 10.6 | 10.6 | 0.26 | 100 | GREY | 4 | CLDY | BLACK <5 CC |
| 25 | LO | 11 | 10 | 360 | 5 | 25 | 7.5 | 10.0 | 0.19 | 75 | GREY | 3 | CLDY | BLACK <5 CC |
| 26 | LO | 11 | 5 | 180 | 1 | 5 | 10 | 10.0 | 0.25 | 100 | GREY | 8 | CLDY | BLACK <5 CC |
| 27 | LO | 11 | 5 | 180 | 2 | 10 | 10 | 10.0 | 0.25 | 100 | GREY | 3 | CLDY | BLACK <5 CC |
| 28 | LO | 11 | 5 | 180 | 10 | 50 | 10 | 10.0 | 0.25 | 100 | GREY | 5 | CLDY | BLACK <5 CC |
| 29 | LO | 11 | 5 | 180 | 5 | 25 | 8.8 | 9.8 | 0.22 | 90 | CLDY | 4 | CLDY | BLACK <5 CC |
| 30 | SO | 17 | 5 | 153 | 5 | 25 | 8.5 | 8.5 | 0.21 | 100 | BLACK YEL | 9 | CLDY | BLACK <5 CC |
| 31 | SO | 17 | 1 | 30.6 | 5 | 25 | 8.5 | 8.5 | 0.21 | 100 | BLACK YEL | 5 | CLDY | BLACK <5 CC |
| 32 | SO | 17 | 2 | 61.2 | 5 | 25 | 8.5 | 8.5 | 0.21 | 100 | BLACK YEL | 5 | CLDY | BLACK <5 CC |
| 33 | SO | 17 | 10 | 306 | 5 | 25 | 8.5 | 8.5 | 0.21 | 100 | BLACK YEL | 10 | CLDY | BLACK <5 CC |
| 34 | SO | 17 | 20 | 612 | 15 | 75 | 7.5 | 7.5 | 0.19 | 100 | GREY COAG | 14 | SL CLDY | BLACK <5 CC |
| 35 | SO | 17 | 20 | 612 | 5 | 25 | 6.5 | 6.5 | 0.16 | 100 | GREY COAG | 13 | SL CLDY | BLACK <5 CC |
| 36 | LO | 11 | 15 | 540 | 5 | 25 | 8 | 8.0 | 0.2 | 100 | GREY YEL | 2 | CLDY | BLACK <5 CC |
| 37 | MCO | 14 | 15 | 540 | 5 | 25 | 8 | 8.0 | 0.2 | 100 | GREY YEL | 4 | CLDY | BLACK <5 CC |
| 38 | SO | 17 | 67 | 2050.2 | 5 | 25 | 18 | 18.0 | 0.25 | 100 | GREY YEL | 45 | CLEAR/FLOC | BLACK <5 CC | x=n in the formula where

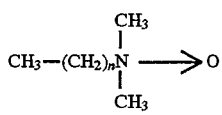

In the following prophetic Examples 2–3, an aqueous cleaning composition containing a 7.5:1 ratio of lauryl dimethyl amine oxide to "AMERZYME-A-100 can be used. In these examples, the surfactant and enzyme combination useful in the method of the present invention is utilized to first remove oil from certain apparatus pursuant to a dispersion mechanism, and thereafter the surfactant and enzyme combination is converted to a stratification composition by merely adjusting the enzyme and surfactant concentration. Thereafter, the oil layer may be separated from the wash water.

EXAMPLE 2

Bilge Cleaning

A 5% active solution of the cleaning compound in water (i.e. 20 parts water to 1 part cleaning compound) can be added to a bilge of a ship at the beginning of a trip. One gallon of cleaning solution is added for every 100 gallons of bilge water expected to accumulate during the trip. The cleaning compound solution mixes with the bilge water due to the ship's motion. The bilge is kept clean and the oil in the bilge water stays dispersed.

At the end of the trip, the bilge contents are pumped to a holding tank for treatment according to the method of the invention.

The concentration of lauryl dimethyl amine oxide and "AMERZYME-A-100" in the bilge water is calculated according to the following equations:

ppm lauryl dimethyl amine oxide =

$$\frac{(\text{amount 5\% cleaning solution used}) \times 44,118}{(\text{amount of bilge water pumped})}$$

and ppm "AMERZYME-A-100" =

$$\frac{(\text{amount 5\% cleaning solution used}) \times 5,882}{(\text{amount of bilge water pumped})}$$

The lauryl dimethyl amine oxide should be present in an amount from about 30–2100 ppm by total solids volume of the bilge water, and most ideally between about 100–300 ppm. The enzyme should be present in an amount between about 1–200 ppm by total solids volume of the bilge water, and most ideally between about 10–30 ppm. If these concentrations are not present, the concentration of the lauryl dimethyl amine oxide and "AMERZYME-A-100" can of course be raised by the addition of these components or reduced by the addition of water. After desired concentrations of lauryl dimethyl amine oxide and "AMERZYME-A-100" have been achieved, the bilge contents are permitted to stand until an oil layer forms on the surface of the water. Additionally, a bottom layer of sludge may form.

The oil and sludge layers my be removed according to any method known by those skilled in the art. For example, the oil may be pumped from the surface using a centrifugal pump equipped with a flexible intake hose. The intake is manually positioned in the oil layer and the oil is pumped to a holding tank. The oil may then be sent to an oil recycling facility for handling. The sludge may be withdrawn through a tap at the lower part of the holding tank wall. The sludge should be disposed of according to local regulations. The remaining bilge water may be put through an oily water separator to remove any remaining oil with no harm to the coalescing media. In the alternative, the remaining water may be suitable for disposal in the local sewer system. However, before disposing of the water in this manner, one should consult with the Industrial Pretreatment Coordinator at the local wastewater treatment plant regarding local regulations.

EXAMPLE 3

In Situ Cleaning Of Heat Exchanger And Column Used In The Petroleum Cracking Process The above-described cleaning composition is diluted to a 0.017% active solution in water (6000 parts water to 1 part cleaning composition). The 0.017% active cleaning composition is added in an amount sufficient to fill the heat exchanger. Live steam or very hot water is circulated, the circulating pump being run for 2 hours. A sample is taken from the reactor to confirm that there is sufficient cleaning composition to clean but not emulsify. A uniform light yellow or amber color indicates too much cleaning solution. Ideally, the sample should have oil droplets and carbon particles in clear water. If the sample is a uniform light yellow to amber color, emulsification has occurred, in which case hot water is added to the system to demulsify. Visual observation of the sample should reveal "deposited" material circulating with the cleaning solution. This cleaning procedure is continued with at least 4 additional sample checks over a 24 hour cleaning period.

Once the wash water from the above-described treatment is removed from the system, it is then treated according to the method of this invention.

As will be readily apparent to those skilled in the art, a wide range of changes and modifications can be made to the preferred embodiments described above. The method of the present invention is not limited to the separation of oleophilic-hydrophobic material from the wash water by-product formed according to the cleaning processes discussed herein. Rather, in a broader sense, the present invention is directed to the separation of oleophilic-hydrophobic material from water, regardless of how such material came to be dispersed therein. The method of this invention is therefore believed applicable to the separation of oleophilic-hydrophobic materials from the widest variety of aqueous systems. It is therefore intended that the foregoing detailed description be regarded as illustrative rather than limiting, and that it be understood that it is the following claims, including all equivalents, which are intended to define the scope of this invention.

We claim:

1. A method of separating oleophilic-hydrophobic material from wash water comprising the steps of:

mixing about 30–2100 ppm surfactant with the wash water wherein the surfactant has the formula:

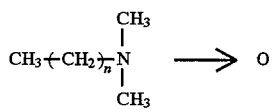

where n is 6–20; and permitting the mixture of wash water and surfactant to stand for a time sufficient for the oleophilic-hydrophobic material to separate.

2. The method of claim 1 wherein the surfactant is selected from the group consisting of lauryl dimethyl amine oxide, stearyl dimethyl amine oxide, myristyl dimethyl amine oxide and mixtures thereof.

3. The method of claim 2 wherein about 100–300 ppm surfactant is mixed with the wash water.

4. A method of separating oil from wash water comprising the steps of:

incorporating with a mixture of wash water and oil about 30 to 2100 ppm of a surfactant having the formula

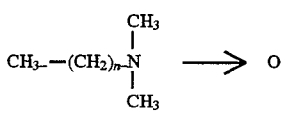

where n is 6–20;

permitting the mixture containing the surfactant to stand in a quiescent state to form an oil phase separate from an aqueous phase, said aqueous phase being more predominantly water than if the surfactant had not been used; and separating the oil phase from the aqueous phase.

5. A method of cleaning industrial equipment containing oil contamination comprising the steps of:

contacting the equipment containing oil contamination with an aqueous solution containing a surfactant having the formula

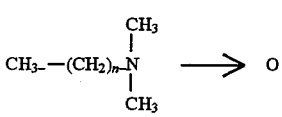

where n is 6 to 20 and agitating the solution in contact with said equipment to thereby remove said oil contamination and provide an oil/water mixture;

permitting the oil/water mixture containing the surfactant to stand in a quiescent state to form an oil phase separate from an aqueous phase, said aqueous phase being more predominantly water than if the surfactant had not been used; and separating the oil phase from the aqueous phase.

6. The method of claim 5, wherein said mixture is permitted to stand in a quiescent state without the incorporation of additional demulsifying agents.

7. The method of claim 5, and including the step of transferring the oil/water mixture to a storage vessel prior to permitting the mixture to stand in a quiescent state.

8. The method of claim 5, and including the step of maintaining the concentration of the surfactant when said mixture is held in the quiescent state at a value of 30 to 2100 ppm.

9. The method of claim 5, and including the step of incorporating steam with said aqueous solution, and the step of agitating the solution comprises circulating the solution and said steam through said equipment.

10. A method of cleaning contaminated industrial equipment comprising the steps of:

contacting industrial equipment containing oil contamination and carbonaceous deposits with an aqueous solution containing a surfactant having the formula

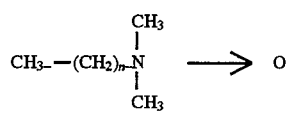

where n is 6 to 20 and agitating the solution in contact with said equipment to thereby remove the oil and dislodge said carbonaceous deposits and provide a water/oil/carbonaceous dispersion;

permitting the water/oil/carbonaceous dispersion containing the surfactant to stand in a quiescent state while maintaining the concentration of the surfactant in said dispersion in the range of 30 to 2100 ppm to thereby form an oil phase and a separate water phase and a separate carbonaceous phase, said water phase being more predominantly water than if the surfactant had not been used, and separating the oil phase and the carbonaceous phase from said water phase.

* * * * *